US012708618B2

(12) United States Patent
Cho et al.

(10) Patent No.: US 12,708,618 B2
(45) Date of Patent: Aug. 18, 2026

(54) PHARMACEUTICAL COMPOSITE FORMULATION COMPRISING PROTON PUMP INHIBITOR AND ANTACID, AND METHOD FOR PREPARING SAME

(71) Applicant: HANMI PHARM. CO., LTD., Hwaseong-si (KR)

(72) Inventors: Hyuk Jun Cho, Uiwang-si (KR); Bo Sik Kim, Seoul (KR); Ho Taek Im, Paju-si (KR); Yong Il Kim, Gwacheon-si (KR)

(73) Assignee: HANMI PHARM. CO., LTD., Hwaseong-si (KR)

( * ) Notice: Subject to any disclaimer, the term of this patent is extended or adjusted under 35 U.S.C. 154(b) by 576 days.

(21) Appl. No.: 18/004,317

(22) PCT Filed: May 21, 2021

(86) PCT No.: PCT/KR2021/006381
§ 371 (c)(1),
(2) Date: Jan. 5, 2023

(87) PCT Pub. No.: WO2022/014848
PCT Pub. Date: Jan. 20, 2022

(65) Prior Publication Data

US 2023/0248707 A1 Aug. 10, 2023

(30) Foreign Application Priority Data

Jul. 14, 2020 (KR) ........................ 10-2020-0087143

(51) Int. Cl.
*A61K 31/4439* (2006.01)
*A61K 9/20* (2006.01)
*A61K 9/24* (2006.01)
*A61K 33/08* (2006.01)

(52) U.S. Cl.
CPC ........ *A61K 31/4439* (2013.01); *A61K 9/2009* (2013.01); *A61K 9/2013* (2013.01); *A61K 9/2027* (2013.01); *A61K 9/2054* (2013.01); *A61K 9/209* (2013.01); *A61K 33/08* (2013.01)

(58) Field of Classification Search
None
See application file for complete search history.

(56) References Cited

U.S. PATENT DOCUMENTS 6,183,776 B1 * 2/2001 Depui .................... A61K 9/209 424/468
6,183,777 B1 2/2001 Chen et al.
7,329,418 B2 * 2/2008 Solomon .............. A61K 9/2072 424/467
9,040,564 B2 5/2015 Ukai et al.
9,321,756 B2 4/2016 Wang et al.
9,833,413 B2 12/2017 Im et al.
2004/0166162 A1 * 8/2004 Niecestro ............... A61K 33/08 514/339
2004/0248939 A1 12/2004 Sugaya et al.
2004/0248942 A1 * 12/2004 Hepburn ................. A61P 43/00 514/338
2010/0143465 A1 6/2010 Thomas et al.
2015/0057314 A1 2/2015 Phillips

FOREIGN PATENT DOCUMENTS

| | | | |
|---|---|---|---|
| EA | 200901169 | A1 | 4/2010 |
| EP | 0813424 | B1 | 11/2002 |
| EP | 4 023 216 | A1 | 7/2022 |
| JP | 2014-510105 | A | 4/2014 |
| KR | 10-2008-0005575 | A | 1/2008 |
| KR | 10-2013-0115593 | A | 10/2013 |
| KR | 10-2015-0067777 | A | 6/2015 |
| KR | 10-2017-0136771 | A | 12/2017 |
| KR | 10-1849125 | B1 | 4/2018 |

OTHER PUBLICATIONS

Bejugam et al. Tablet formulation of an active pharmaceutical ingredient with a sticking and filming problem: direct compression and dry granulation evaluations, Drug Dev Ind Pharm, 2015; 41(2): 333-341 (Year: 2015).*
Communication dated Mar. 31, 2023 issued by the Korean Patent Office in application No. 10-2020-0087143.
Russian Search Report issued Feb. 16, 2024 in Application No. 2022133378/04.
I.S. Chekman, et al., "Pharmacology. Prescription. Practical exercises: Textbook for foreign students," 2003, pp. 24-25 (2 pages total).
T.V. Stolbova , "Pharmaceutical chemistry: Textbook / FGBOU VO Primorskaya State Agricultural Academy," 2016, p. 9 (2 pages total).
D.A. Kharkevich, "Pharmacology: Textbook ," 2010, pp. 72-82 (13 pages total).
Russian Office Action issued Feb. 19, 2024 in Application No. 2022133378/04.
Saudi Arabian Office Action issued Feb. 19, 2024 in Application No. 523442138.
Extended European Search Report dated Apr. 16, 2024 in Application No. 21841376.3.
International Search Report of PCT/KR2021/006381 dated Sep. 2, 2021 [PCT/ISA/210].

(Continued)

*Primary Examiner* — Sahana S Kaup
*Assistant Examiner* — Ashlee E Wertz
(74) *Attorney, Agent, or Firm* — Sughrue Mion, PLLC

(57) ABSTRACT

Provided are a pharmaceutical composite formulation and a method of preparing the same, the pharmaceutical composite formulation including: a first layer containing, as an active ingredient, a proton pump inhibitor or a pharmaceutically acceptable salt thereof and a lubricant, and a second layer containing, as an active ingredient, an antacid selected from magnesium hydroxide, magnesium oxide, and a mixture thereof.

7 Claims, 1 Drawing Sheet

(56) References Cited

OTHER PUBLICATIONS

I.S. Chekman, et al., "Pharmacology. Prescription. Practical exercises: Textbook for foreign students," pp. 24-25 (2 pages total).
T.V. Stolbova , Pharmaceutical chemistry: Textbook / FGBOU VO Primorskaya State Agricultural Academy, p. 9 (2 pages total).
Communication dated Jul. 8, 2025 in Brazilian Application No. BR112023000520-5.
Communication issued Jan. 7, 2026 in European Patent Application No. 21841376.3.

* cited by examiner

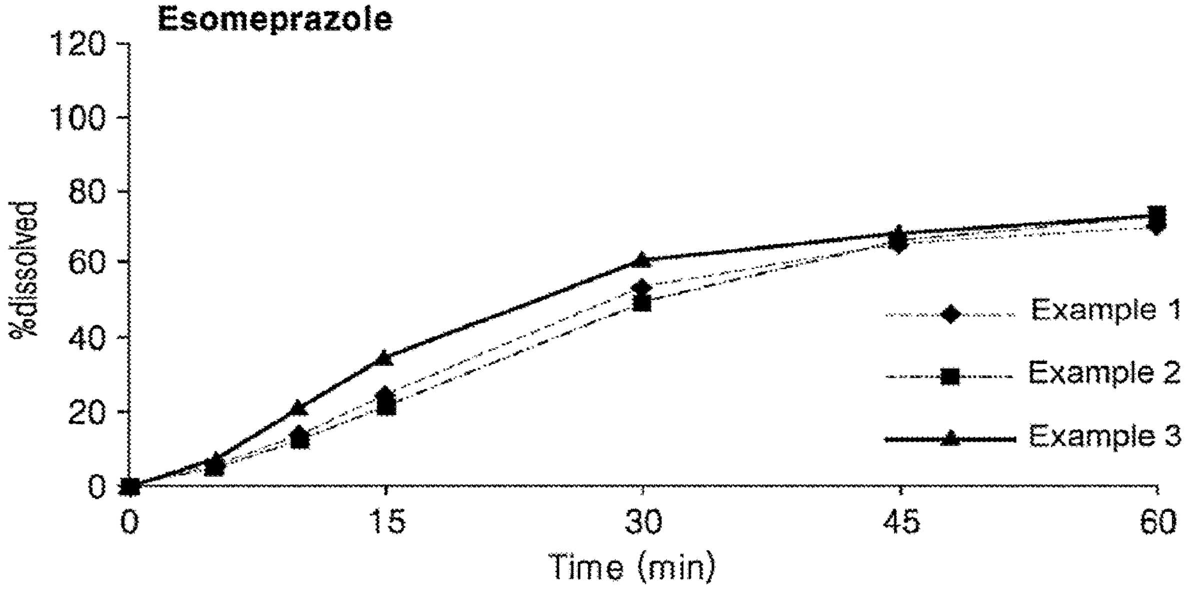
Esomeprazole
120
100
80
60
40
20
0
%dissolved
0
15
30
45
60
Time (min)
Example 1
Example 2
Example 3

PHARMACEUTICAL COMPOSITE FORMULATION COMPRISING PROTON PUMP INHIBITOR AND ANTACID, AND METHOD FOR PREPARING SAME

TECHNICAL FILED

The disclosure relates to a pharmaceutical composite formulation including a proton pump inhibitor and an antacid, and more specifically, to a pharmaceutical composite formulation with improved pharmaceutical quality, physical stability, and productivity while preventing gastric degradation of proton pump inhibitors and improving stability from gastric acid without enteric coating, and a method of preparing the same.

BACKGROUND ART

A proton pump inhibitor is a drug that inhibits the proton pump (H+/K+-ATPase) of parietal cells to suppress production of hydrochloric acid and weaken acidity in the digestive system. A proton pump inhibitor has medicinal effects on indigestion, gastroesophageal reflux disease, pharyngeal reflux disease, or peptic ulcer disease. In particular, a benzimidazole-based compound or a salt thereof is used as a therapeutic agent for peptic ulcer having a proton pump inhibitory action. Examples thereof include omeprazole, lansoprazole, rabeprazole, pantoprazole, and esomeprazole.

However, such proton pump inhibitors have a problem in that the proton pump inhibitors are easily decomposed or deformed under acidic conditions. For example, lansoprazole is poorly soluble in water and is very unstable to acid, and thus, lansoprazole is easily decomposed in gastric juice, an acidic solution, and does not exhibit the desired pharmacological effect. In addition, esomeprazole has a problem in that the physical properties and storage stability of the free base itself are not good, and in particular, stability in acidic and neutral environments is significantly lower than stability in alkaline environments. Esomeprazole magnesium salt is also greatly affected by stability of the drug depending on the additive or preparation method, and the stability thereof is poor particularly in an acidic environment.

As a formulation to improve the stability of benzimidazole-based proton pump inhibitors, enteric formulations for dissolution and absorption in the intestine, by introducing an enteric coating layer to prevent exposure to gastric acid in the stomach and to prevent drug degradation, have been studied. For example, Korean Patent Publication No. 10-2008-0005575 proposes a method of stabilizing by coating with an enteric polymer to improve the stability of benzimidazole-based proton pump inhibitors.

However, when a drug is prepared in this manner, a relatively large amount of an enteric polymer or an excessive amount of additives is required, and when the enteric coating layer is lost, the drug is easily exposed to gastric acid, and decomposition cannot be prevented. In addition, there is a disadvantage in that the onset time of the drug is delayed, and productivity is also poor. Therefore, it is required to develop a formulation that may improve the stability of proton pump inhibitors in gastric acid environment, provide rapid drug effect, and improve drug quality, physical stability, and productivity at the same time.

DESCRIPTION OF EMBODIMENTS

Technical Problem

An aspect provides a pharmaceutical composite formulation including a proton pump inhibitor or a pharmaceutically acceptable salt thereof and an antacid and having improved pharmaceutical quality, physical stability, and productivity.

Provided is a composite formulation that may solve problems that are likely to occur due to the characteristics of proton pump inhibitors such as esomeprazole and antacids such as magnesium hydroxide or magnesium oxide included in the composite formulation, for example, reduced formulation uniformity, tableting disorder, and breakage, which may be likely to occur during bulk formulation, filling or tableting for formulation.

Another aspect provides a method for preparing a pharmaceutical composite formulation including a proton pump inhibitor or a pharmaceutically acceptable salt thereof and an antacid.

Solution to Problem

An aspect provides a pharmaceutical composite formulation comprising a first layer comprising, as an active ingredient, a proton pump inhibitor or a pharmaceutically acceptable salt thereof and a lubricant, and a second layer comprising, as an active ingredient, an antacid selected from magnesium hydroxide, magnesium oxide, and a mixture thereof.

Another aspect provides a method of preparing a pharmaceutical composite formulation comprising preparing a first layer mixed part comprising, as an active ingredient, a proton pump inhibitor or a pharmaceutically acceptable salt thereof and a lubricant, and preparing a second layer mixed part comprising, as an active ingredient, an antacid selected from magnesium hydroxide, magnesium oxide, and a mixture thereof, and tableting the first layer mixed part and the second layer mixed part.

Advantageous Effects of Disclosure

The pharmaceutical composite formulation according to an aspect may improve tableting disorders, improve drug quality and productivity, and improve physical stability. The composite formulation may prevent the dissolution of proton pump inhibitors by gastric acid without enteric coating, wherein the proton pump inhibitors rapidly dissolute and are absorbed in a body, and the onset of drug efficacy is not delayed.

The method of preparing the composite formulation according to an aspect may improve in tableting disorder, quality, and stability.

BRIEF DESCRIPTION OF DRAWINGS

FIG. 1 is a graph of dissolution rates (%) of esomeprazole versus dissolution time (minutes) of composite formulations prepared in Examples 1 to 3.

MODE

Hereinafter, the disclosure will be described in more detail.

All technical terms used herein have the same meaning as commonly understood by one of ordinary skill in the art, unless defined otherwise. In addition, although preferred methods or samples are described herein, similar or equivalent ones also fall within the scope of the present specification. In addition, the numerical values described herein are considered to include the meaning of "about" even if not specified. The contents of all publications incorporated herein by reference are hereby incorporated by reference in their entirety.

An aspect provides a pharmaceutical composite formulation comprising a first layer comprising, as an active ingredient, a proton pump inhibitor or a pharmaceutically acceptable salt thereof and a lubricant, and a second layer comprising, as an active ingredient, an antacid selected from magnesium hydroxide, magnesium oxide, and a mixture thereof.

A pharmaceutical composite formulation is formulated in a certain shape by mixing and molding active ingredients and pharmaceutical additives. Here, the physicochemical properties of the active ingredient or the composition of the composite formulation including the active ingredient and pharmaceutical additives may affect the quality, physical stability, and productivity of the drug.

Tableting disorders that may occur during the preparation of pharmaceutical composite formulations include sticking, capping, laminating, chipping, or picking. Such tableting disorder not only affects the quality of pharmaceuticals, but also causes continuous production work not to be possible, which may cause a decrease in productivity.

Moreover, in case of preparing a tablet to show effects of preventing acid decomposition of proton pump inhibitor (PPI) in a low pH environment of gastric juice in a body, a binder is included in the first layer for a time difference release of PPI and antacid, that is, the prior release of PPI, the occurrence of tableting disorder may increase. In the composite formulation according to one embodiment, such tableting disorder may be remarkably improved through granulation of the first layer and control of a lubricant content.

In addition, when an antacid such as magnesium hydroxide or magnesium oxide is included in a high ratio as an active ingredient included in the composite formulation, the tableting property may be worse, and the hardness is lowered, and thus the tablet may be like to be broken. In the composite formulation according to one embodiment, the physical stability may be remarkably improved by adjusting the length ratio of the major axis to the minor axis of the composite formulation.

The term "sticking" as used herein refers to a phenomenon in which powder adheres to a surface of a punch during a preparation process, and a groove is formed on a surface of a tablet. During tableting, powder may adhere to a surface of an upper punch or lower punch, resulting in grooves on a surface of a tablet.

The term "capping" as used herein refers to a phenomenon in which an upper part of a tablet is peeled off in a shape of a hat. The term "laminating" as used herein refers to a phenomenon in which a tablet is peeled off in layers. The term "picking" as used herein refers to a phenomenon in which uneven spots appear on a surface of a tablet.

Tableting disorders that may occur during the preparation of the composite formulation according to an embodiment may include sticking, capping, laminating, and picking.

The first layer in the composite formulation may be prepared from a mixed part comprising a proton pump inhibitor or a pharmaceutically acceptable salt thereof and a lubricant. The mixed part may further include another pharmaceutical additive.

For example, the first layer may further include a binder. In an embodiment, the first layer may further include any one binder selected from hydroxypropyl cellulose, hypromellose, polyvinylpyrrolidone, pregelatinized starch, and any combination thereof. The content of the binder included in the first layer of the composite formulation may be in an amount sufficient to prevent the initial release of a proton pump inhibitor included in the first layer of the composite formulation, preventing acid degradation of the proton pump inhibitor in the stomach and dissoluting of about 55% or more of the proton pump inhibitor for 60 minutes during dissolution test measurement. In addition, the content of the binder included in the first layer of the composite formulation may be in an amount exceeding about 2 parts by weight and less than 6 parts by weight based on 1 part by weight of a disintegrant included in the first layer. For example, the binder included in the first layer of the composite formulation may be about 2 parts to 5.5 parts by weight, for example, about 2.5 parts to 5 parts by weight, or about 2 parts to 5 parts by weight, based on 1 part by weight of a disintegrant included in the first layer. When the binder is included within this range, the time difference release according to layer of a proton pump inhibitor and an antacid present in different layers in the composite formulation may be secured, and thus, the antacid is released first from the composite formulation, and then the proton pump inhibitor is then released. Therefore, it is possible to prevent gastric acid degradation of the drug and obtain a desired dissolution rate of the proton pump inhibitor.

In an embodiment, the first layer including the proton pump inhibitor and the lubricant may be in a form of granules. The granules may be dry granules or wet granules, preferably dry granules.

For example, the granules may be prepared by a method of compacting. The compacting may be prepared using a roller compactor. For example, the compacting may be performed under conditions of hydraulic pressure of about 1 MPa to 7 MPa, a feeder speed of about 1 rpm to 10 rpm, and a roller speed of about 0.5 rpm to 5 rpm to form flakes. Accordingly, granules may be obtained by pulverizing and sieving the prepared compact. For example, the sieving may be performed with a sieve of about 0.5 mm to 5 mm sieve size.

As the pharmaceutical composite formulation includes the first layer in the form of the granules, it is possible to significantly improve productivity by reducing tableting disorder, including sticking, that may occur during the preparation of the composite formulation.

The term "lubricant" as used herein refers to a material used to provide slippage and reduce friction when preparing a formulation. The lubricant may improve fluidity of the powder and granules to increase filling properties to a die, which is a lower part of a tablet machine, and reduce friction between the powder and the granules and between the powder and the punch-die, which are respectively an upper part and a lower part of the tablet machine, to thereby facilitating compressing and releasing of the tablet.

The lubricant may be at least one selected from the group consisting of sodium stearyl fumarate, stearic acid, stearate, talc, corn starch, carnauba wax, light anhydrous silicic acid, magnesium silicate, synthetic aluminum silicate, hydrogenated oil, white wax, titanium oxide, microcrystalline cellulose, macrogol 4000 and 6000, isopropyl myristate, calcium hydrogen phosphate, talc, and any mixture thereof, but embodiments are not limited thereto. In one embodiment, the lubricant included in the first layer of the composite formulation may be sodium stearyl fumarate, magnesium stearate, or any combination thereof.

In some embodiments, the lubricant included in the first layer of the composite formulation may be included in a range of about 1.5 wt % to 7 wt %, for example, about 2 wt % to 6.5 wt %, or for example, about 3 wt % to 6 wt % based on a total weight of the first layer. For example, the lubricant may be included in a range of about 3 wt % to 5.5 wt %, about 3 wt % to 5 wt %, or about 3.5 wt % to 5.5 wt % based on a total weight of the first layer.

As the pharmaceutical composite formulation includes the lubricant in this range, it is possible to significantly improve productivity by reducing tableting disorder, including sticking, that may occur during the preparation of the composite formulation.

In one embodiment, when a total weight of the first layer is 1 part by weight, a total weight of the second layer may be about 4 parts by weight or less, and more specifically, about 3.5 parts by weight or less. For example, when a total weight of the first layer is 1 part by weight, the second layer of the composite formulation may be less than about 3.25 parts by weight. For example, when a total weight of the first layer of the composite formulation is 1 part by weight, the second layer may be about 1 part to 4 parts by weight.

In one embodiment, the first layer and the second layer of the pharmaceutical composite formulation may be included in a weight ratio of about 1:4 to 1:1 or about 1:3.5 to 1:1. For example, a weight ratio of the first layer to the second layer may be about 1:3.25 to 1:1.

As the pharmaceutical composite formulation includes the weight or weight ratio of the first layer and the second layer in this range, various tableting disorders including sticking are reduced, the formulation uniformity of the composite formulation is significantly improved, and the quality and productivity of pharmaceuticals are improved. When the weight ratio is out of this range, the content uniformity may be deteriorated due to the difference in the mass of each layer.

In an embodiment, the composite formulation may be a tablet or a capsule. For example, the composite formulation may be a multi-layer tablet such as a double-layer tablet or a three-layer tablet, or a tablet in tablet (nucleated tablet) form, preferably a double-layer tablet. Such a tablet may have a hardness of, for example, about 10 kP to about 20 kP.

The pharmaceutical composite formulation may be oval, round, semicircular, or square, preferably oval.

It is necessary to secure physical stability of pharmaceutical preparations to prevent damage that may occur during handling, transportation, or preservation of pharmaceuticals and to maintain the quality of pharmaceuticals. As the pharmaceutical composite formulation according to one embodiment contains magnesium hydroxide or magnesium oxide used as an antacid as one of the active ingredients in a high ratio, tablet breakage may easy occur. In addition, when a double-layer tablet consisting of a layer containing esomeprazole and a layer containing magnesium hydroxide is taken, disintegration and release of the magnesium hydroxide-containing layer in intragastric environment is great, and thus, there is a difference in stability between the two layers constituting the double-layer tablet, thus being vulnerable to external shocks.

In general, a binder may be added to maintain the structure of the formulation and reduce breakage. However, as using a binder in the layer containing magnesium hydroxide may limit prior release of antacid, the antacid may be released earlier than proton pump inhibitors and neutralize gastric acid, thus, hindering breakdown of the proton pump inhibitors in the stomach. Therefore, even when tablet breakage occurs, there is a limit to the use of a binder in the layer containing magnesium hydroxide.

The present inventors studied the form of the formulation capable of improving the physical stability of the pharmaceutical formulation, and found that it is possible to improve formulation stability and reduce breakage by adjusting the length ratio of major axis to minor axis.

The term "major axis" as used herein refers to a longest length of a composite formulation, such as a tablet, according to an embodiment when viewed from above. The term "minor axis" as used herein refers to a shortest length of a composite formulation, such as a tablet, according to an embodiment when viewed from above.

The composite formulation may have two orthogonal axes of equal or different lengths when projected onto a flat surface, with a longer length being the major axis and a shorter length being the minor axis. When two orthogonal axes have the same length, one may be used as a major axis and the other as a minor axis.

The pharmaceutical composite formulation according to one embodiment significantly improves the physical stability of the pharmaceutical formulation and reduces damage that may occur during the handling, transportation, or preservation of pharmaceuticals by adjusting the length of the major and minor axes, thereby improving quality and productivity of pharmaceuticals.

The composite formulation may have the same length ratio of the major and minor axes, or may have different shapes. The composite formulation may have a length ratio of major axis to minor axis of about 2.35:1 or less. For example, the length of a major axis of the composite formulation may not be greater than about 2.3 times the length of a minor axis. For example, the length of a major axis of the composite formulation may not be greater than about 2.25 times the length of a minor axis. For example, a length ratio of major axis to minor axis in the composite formulation may be about 1:1 to 2.3:1. For example, a length ratio of major axis to minor axis in the composite formulation may be about 1:1 to 2.25:1. In an embodiment, the composite formulation may be a double-layer tablet having a length ratio of major axis to minor axis of about 1:1 to 2.3:1. For example, in the composite formulation, a major axis may be in a range of about 14 mm to 16 mm, and a minor axis may be in a range of about 7.2 mm to 8 mm.

A composite formulation having a length ratio of major axis to minor axis in a range according to one embodiment may have a failure rate of about 10% or less. For example, the composite formulation according to one embodiment may have a failure rate of about 0%.

In comparison, physical stability may be reduced in composite formulations where the length ratio of the major axis to minor axis exceeds about 2.35:1. For example, the failure rate may be greater than about 10%, about 15% or more, or about 15% to 50%. For example, a composite formulation with a length ratio of the major axis:minor axis of 2.36:1 may have a failure rate of about 16.7%, and a composite formulation with the length ratio of 2.5:1 may have a failure rate of about 30%.

The failure rate may be measured by counting the number of broken tablets after placing 30 composite formulation tablets in a high density polyethylene (HDPE) bottle and dropping 10 times from a height of 150 cm.

In an embodiment, the proton pump inhibitor may be any one selected from esomeprazole, omeprazole, lansoprazole, rabeprazole, pantoprazole, and any combination thereof. For example, the proton pump inhibitor included in the first layer of the pharmaceutical composite formulation may be in a range of about 5 wt % to 25 wt % based on the total weight of the first layer.

The pharmaceutically acceptable salt of the proton pump inhibitor may be any pharmaceutically acceptable salt that may be used in the related art, for example, an ammonium salt or a metal salt, such as a magnesium (Mg) salt, a strontium (Sr) salt, a lithium salt, a sodium salt, a potassium salt, or a calcium salt may be used, but is not limited thereto.

The proton pump inhibitor or a pharmaceutically acceptable salt thereof may be provided in a form of an anhydride or a hydrate, such as a monohydrate, a dihydrate, or a trihydrate.

For example, an antacid selected from magnesium hydroxide, magnesium oxide, and a mixture thereof included in the second layer of the pharmaceutical composite formulation may be in a range of about 50 wt % to 90 wt % based on the total weight of the second layer.

In an embodiment, the first layer may further include any one selected from a diluent, a binder, a disintegrant, and any mixture thereof.

In an embodiment, the second layer may further include any one selected from a diluent, a disintegrant, a fluidizing agent, a lubricant, or any mixture thereof.

The term "diluent" as used herein refers to a substance added to increase a dose of a formulation. Unlike active pharmaceuticals, a diluent may be a safe substance used to increase stability and also referred to as excipients. The diluent may be at least one selected from the group consisting of microcrystalline cellulose, lactose, dextrin, mannitol, sorbitol, starch, calcium hydrogen phosphate, anhydrous calcium hydrogen phosphate, calcium carbonate, saccharide, and a mixture thereof, but is not limited thereto. For example, the diluent may be microcrystalline cellulose. For example, the diluent included in the first layer of the pharmaceutical composite formulation may be in a range of about 50 wt % to 90 wt % based on the total weight of the first layer. For example, the diluent included in the second layer of the pharmaceutical composite formulation may be in a range of about 7 wt % to 40 wt % based on the total weight of the second layer.

The term "binder" as used herein refers to a substance added to impart a certain adsorption or solidification to a mixture. The binder may be at least one selected from the group consisting of hydroxypropyl cellulose, hypromellose (hydroxypropyl methyl cellulose), polyvinylpyrrolidone, pregelatinized starch, and any mixture thereof, but is not limited thereto. For example, the binder may be hydroxypropyl cellulose. For example, the binder included in the first layer of the pharmaceutical composite formulation may be in a range of about 1 wt % to 20 wt % based on the total weight of the first layer.

The term "disintegrant" as used herein refers to a substance added to expand a formulation such that a solid material is disintegrated before absorption. The disintegrant may be at least one selected from the group consisting of crospovidone, sodium starch glycolate, and a mixture thereof, but is not limited thereto. For example, the disintegrant may be crospovidone. For example, the disintegrant included in the first layer of the pharmaceutical composite formulation may be in a range of about 1 wt % to 5 wt % based on the total weight of the first layer. The content of the disintegrant included in the first layer of the composite formulation may be in an amount sufficient to prevent acid degradation of a proton pump inhibitor included in the first layer of the composite formulation in the stomach and dissolute of about 55% or more of the proton pump inhibitor for 60 minutes during dissolution test measurement. For example, the disintegrant included in the second layer of the pharmaceutical composite formulation may be in a range of about 1 wt % to 5 wt % based on the total weight of the second layer.

The term "fluidizing agent" as used herein refers to a substance that affects flow of a formulation. The fluidizing agent may be at least one selected from the group consisting of colloidal silicon dioxide, silicon dioxide, talc, and a mixture thereof, but is not limited thereto. For example, the fluidizing agent may be colloidal silicon dioxide. For example, the fluidizing agent included in the second layer of the pharmaceutical composite formulation may be in a range of about 1 wt % to 5 wt % based on the total weight of the second layer.

The lubricant component included in the second layer of the composite formulation may be identical to as the lubricant component included in the first layer. For example, the lubricant included in the first and second layers of the composite formulation may be sodium stearyl fumarate. The lubricant included in the second layer of the pharmaceutical composite formulation may be in a range of about 0.1 wt % to 3 wt % based on the total weight of the second layer.

Additionally, any pharmaceutical excipients commonly used in the art may be included in an appropriate content. For example, at least one additive selected from the group consisting of surfactants, antioxidants, preservatives, stabilizers, flavoring agents, colorants, solubilizers, pH adjusting agents, coating agents, and any combination thereof may be additionally included, but is not limited thereto.

In the composite formulation, proton pump inhibitors and antacids in different layers may show time-difference release between layers. For example, in the composite formulation, antacid present in an antacid-containing layer may be first released to increase an intragastric pH, and then, as a proton pump inhibitor present in a layer containing the proton pump inhibitor is released, acidic environment in the stomach may be neutralized, thus preventing decomposition of the proton pump inhibitor by gastric acid.

As the composite formulation is a pharmaceutical composite formulation that includes a proton pump inhibitor and an antacid as active ingredients, the antacid rapidly neutralizes gastric acid. Thus, unlike commercially available enteric formulations, decomposition of the proton pump inhibitor may be prevented without enteric coating, stability from gastric acid may be improved, and the proton pump inhibitor may be rapidly dissoluted and absorbed in a body, thus not delaying the drug effect.

In an embodiment, in the composite formulation, when a mixed solution of 150 mL of 0.1 N HCl and 450 mL of purified water is tested under conditions of 75 rpm and 37±0.5° C. according to the second paddle method of the US Pharmacopoeia (USP) dissolution test item, a dissolution rate of the proton pump inhibitor for 60 minutes may be 55% or higher. In an embodiment, a dissolution rate of the composite formulation may be about 70% or higher.

Another aspect provides a method of preparing a pharmaceutical composite formulation including: preparing a first layer mixed part including, as an active ingredient, a proton pump inhibitor or a pharmaceutically acceptable salt thereof and a lubricant, and preparing a second layer mixed part including an antacid selected from magnesium hydroxide, magnesium oxide, and a mixture thereof; and tableting the first layer mixed part and the second layer mixed part.

In one embodiment, the preparing of the first layer mixed part may include a granulation (compacting) process. The compacting method may be the same as described in relation to the pharmaceutical composite formulation.

In the present specification, the numerical range indicated by using the term "to" refers to a range including the numerical values described before and after the term as the lower limit and the upper limit, respectively. The terms "about or expressions such as "approximately" mean that a described value may vary to some extent. For example, the value may vary by 10%, 5%, 2%, or 1%. For example, "about 5" is meant to include any value between 4.5 and 5.5, between 4.75 and 5.25, or between 4.9 and 5.1, or between 4.95 and 5.05.

The terms "has", "may have", "comprises", or "may include" indicate the presence of a corresponding feature (e.g., a numerical value or a component such as an ingredient), and does not exclude the presence of additional features.

EXAMPLES

Examples 1 to 3: Preparation of Double-Layer Tablet Including Esomeprazole and Magnesium Hydroxide According to the compositions shown in Table 1, double-layer tablets including, as active ingredients, esomeprazole and magnesium hydroxide as an antacid were prepared.

Esomeprazole, microcrystalline cellulose, hydroxypropyl cellulose, and crospovidone were taken and mixed for 10 minutes. Flakes were formed by compressing the mixture using a roller compactor (TF-1-A60, Freund vector) under the conditions of a hydraulic pressure of 2 MPa, a feeder speed of 5 rpm, and a roller speed of 1 rpm. Then, the flakes were established through a sieve of 1.0 mm sieve size. Sodium stearyl fumarate was added thereto as a lubricant and mixed for 5 minutes to prepare a final mixed part of the upper layer.

Magnesium hydroxide, microcrystalline cellulose, and crospovidone were taken and mixed for 10 minutes. Flakes were formed by compressing the mixture using a roller compactor (TF-1-A60, Freund vector) under the conditions of a hydraulic pressure of 5 MPa, a feeder speed of 5 rpm, and a roller speed of 1 rpm. Then, the flakes were established through a sieve of 2.0 mm sieve size. After adding colloidal silicon dioxide as a fluidizing agent to the sieved product and mixing for 5 minutes, sodium stearyl fumarate as a lubricant was added thereto and mixed for 5 minutes to prepare a final mixed part of the lower layer.

A double-layer tablet (having a hardness of about 17 kp) was prepared by tableting the final mixed part of the upper layer and the final mixed part of the lower layer with a tablet machine (Autotab-200TR, Ichihashi Seiki) and an oval punch with a width of 15.5 mm and a length of 7.5 mm.

The composition of the pharmaceutical composite formulation according to Examples 1 to 3 are shown in Table 1.

TABLE 1

| Process | Component (unit: mg) | Example 1 | Example 2 | Example 3 |
|---|---|---|---|---|
| Compacting | Esomeprazole magnesium trihydrate | 22.25 | 22.25 | 44.5 |
| | Microcrystalline cellulose | 113.75 | 113.75 | 227.5 |
| | Hydroxypropyl cellulose | 16.0 | 16.0 | 32.0 |
| | Crospovidone | 4.0 | 4.0 | 8.0 |
| Final mixing | Sodium stearyl fumarate | 9.0 | 6.0 | 18.0 |
| Total of upper layer | | 165.0 | 162.0 | 330.0 |
| Compacting | Magnesium hydroxide | 350.0 | 350.0 | 350.0 |
| | Microcrystalline cellulose | 135.0 | 135.0 | 135.0 |
| | Crospovidone | 15.0 | 15.0 | 15.0 |
| Final mixing | Colloidal silicon dioxide | 15.0 | 15.0 | 15.0 |
| | Sodium stearyl fumarate | 5.0 | 5.0 | 5.0 |
| Total of lower layer | | 520.0 | 520.0 | 520.0 |
| Total of uncoated tablet | | 685.0 | 682.0 | 850.0 |

Examples 4 and 5: Preparation of Double-Layer Tablet Including Esomeprazole and Magnesium Hydroxide Double-layer tablets were produced in Examples 4 and 5 with the same hardness of about 17 kp as Example 1 by using the final mixed part of the upper layer and the final mixed part of the lower layer of Example 1, except that the punch was changed.

In Example 4, a double-layer tablet was prepared by tableting with an oval punch with a width of 14.0 mm and a length of 8.0 mm.

In Example 5, a double-layer tablet was prepared by tableting with an oval punch with a width of 16.0 mm and a length of 7.2 mm.

COMPARATIVE EXAMPLES

Comparative Examples 1 to 6: Preparation of Double-Layer Tablet Including Esomeprazole and Magnesium Hydroxide As the compositions shown in Tables 2 and 3, esomeprazole, microcrystalline cellulose, hydroxypropyl cellulose, and crospovidone were taken and mixed for 10 minutes. Sodium stearyl fumarate as a lubricant was added thereto and mixed for 5 minutes to prepare a final mixed part of the upper layer. Unlike Example 1, the upper layer of Comparative Examples 1 to 3 did not undergo a granulation process (compacting) of the mixture.

Magnesium hydroxide, microcrystalline cellulose, and crospovidone were taken and mixed for 10 minutes. Flakes were formed by compressing the mixture using a roller compactor (TF-1-A60, Freund vector) under the conditions of a hydraulic pressure of 5 MPa, a feeder speed of 5 rpm, and a roller speed of 1 rpm. Then, the flakes were established through a sieve of 2.0 mm sieve size. After adding colloidal silicon dioxide as a fluidizing agent to the sieved product and mixing for 5 minutes, sodium stearyl fumarate as a lubricant was added thereto and mixed for 5 minutes to prepare a final mixed part of the lower layer.

Double-layer tablets were prepared using a tablet machine (Autotab-200TR, Ichihashi Seiki) as in Example 1 using the final mixed part of the upper layer and the final mixed part of the lower layer.

The composition of the pharmaceutical composite formulation according to Comparative Examples 1 to 6 are shown in Tables 2 and 3.

TABLE 2

| Process | Component (unit: mg) | Comparative Example 1 | Comparative Example 2 | Comparative Example 3 |
|---|---|---|---|---|
| Mixing | Esomeprazole magnesium trihydrate | 22.25 | 22.25 | 22.25 |
| | Microcrystalline cellulose | 113.75 | 113.75 | 113.75 |
| | Hydroxypropyl cellulose | 16.0 | 16.0 | 16.0 |
| | Crospovidone | 4.0 | 4.0 | 4.0 |

TABLE 2-continued

| Process | Component (unit: mg) | Comparative Example 1 | Comparative Example 2 | Comparative Example 3 |
|---|---|---|---|---|
| Final mixing | Sodium stearyl fumarate | 9.0 | 12.0 | 15.0 |
| | Total of upper layer | 165.0 | 168.0 | 171.0 |
| Compacting | Magnesium hydroxide | 350.0 | 350.0 | 350.0 |
| | Microcrystalline cellulose | 135.0 | 135.0 | 135.0 |
| | Crospovidone | 15.0 | 15.0 | 15.0 |
| Final mixing | Colloidal silicon dioxide | 15.0 | 15.0 | 15.0 |
| | Sodium stearyl fumarate | 5.0 | 5.0 | 5.0 |
| | Total of lower layer | 520.0 | 520.0 | 520.0 |
| | Total of uncoated tablet | 685.0 | 688.0 | 691.0 |

TABLE 3

| Process | Component (unit: mg) | Comparative Example 4 | Comparative Example 5 | Comparative Example 6 |
|---|---|---|---|---|
| Compacting | Esomeprazole magnesium trihydrate | 22.25 | 13.5 | 16.9 |
| | Microcrystalline cellulose | 113.75 | 68.9 | 86.2 |
| | Hydroxypropyl cellulose | 16.0 | 9.7 | 12.1 |
| | Crospovidone | 4.0 | 2.4 | 3.0 |
| Final mixing | Sodium stearyl fumarate | 2.0 | 5.5 | 6.8 |
| | Total of upper layer | 158.0 | 100.0 | 125.0 |
| Compacting | Magnesium hydroxide | 350.0 | 350.0 | 350.0 |
| | Microcrystalline cellulose | 135.0 | 135.0 | 135.0 |
| | Crospovidone | 15.0 | 15.0 | 15.0 |
| Final mixing | Colloidal silicon dioxide | 15.0 | 15.0 | 15.0 |
| | Sodium stearyl fumarate | 5.0 | 5.0 | 5.0 |
| | Total of lower layer | 520.0 | 520.0 | 520.0 |
| | Total of uncoated tablet | 678.0 | 620.0 | 645.0 |

TEST EXAMPLES

Test Example 1: Assessment of Tableting Disorder and Confirmation of Occurrence of Sticking About 500 tablets of the double-layer tablets of Examples 1 and 2 and Comparative Examples 1 to 4 were tested during the tableting process, and the results are shown in Table 4. In Examples 1 and 2, tableting failures such as sticking, capping, laminating, and picking did not occur. In Comparative Examples 1 to 4, sticking occurred.

TABLE 4

| | Example 1 | Example 2 | Comparative Example 1 | Comparative Example 2 | Comparative Example 3 | Comparative Example 4 |
|---|---|---|---|---|---|---|
| Upper layer process | Compacting | Compacting | Mixing | Mixing | Mixing | Compacting |
| Amount of lubricant in upper layer | 5.5 wt % | 3.7 wt % | 5.5 wt % | 7.1 wt % | 8.8 wt % | 1.3 wt % |
| Sticking | did not occur | did not occur | occurred after tableting 200 tablets | occurred after tableting 200 tablets | occurred after tableting 200 tablets | occurred after tableting 350 tablets |

As a lubricant, sodium stearyl fumarate was used. When a tableting failure such as sticking occurs, continuous production of tablets becomes impossible. Therefore, the degree of tableting failure was determined based on the number of tablets produced until the time of sticking.

In Comparative Examples 1 to 3, double-layer tablets were produced by using the final mixed part of the upper layer that underwent a direct pressing process after the mixing process, which is a simple process without granulation. In Comparative Examples 1 to 3, some of the upper layer stuck to the punch during tableting, and even when sodium stearyl fumarate was increased to about 9 wt %, there was no improvement in the tableting disorder.

On the other hand, in Examples 1 and 2, where a compacting process was included, even when about 500 tablets were produced, tableting failure, including sticking, did not occur, thus improving productivity.

In Comparative Example 4, in which sodium stearyl fumarate was reduced to about 1.3 wt %, sticking occurred, but it was confirmed that sticking was improved as compared with Comparative Examples 1 to 3 where the direct pressing process was used. Therefore, it was confirmed that tableting disorders including sticking may be improved when the compacting process is applied.

Test Example 2: Formulation Uniformity Test of Esomeprazole

Each of 10 double-layer tablets prepared in Examples 1 and 3 and Comparative Examples 5 and 6 were used to perform the content uniformity test among the formulation uniformity clause, and the results are shown in Table 5.

<Analysis Condition>

Column: Inertsil ODS-3V 150 mm×4.6 mm, 5 μm

Column temperature: at a certain temperature around 25° C.

Mobile phase: acetonitrile:phosphate buffer solution (pH 7.3):water=350:500:150 (pH 7.3 phosphate buffer solution: 10.5 mL of 1.0 M sodium dihydrogen phosphate and 60.0 mL of 0.5 M disodium hydrogen phosphate were mixed together, and 1,000 mL of purified water was added thereto.)

Detector: Ultraviolet absorption spectrometer (measurement wavelength: 302 nm)

Flow rate: 1.0 milliliter per minute (mL/min)

Injection amount: 20 μL

TABLE 5

| | Example 1 | Example 3 | Comparative Example 5 | Comparative Example 6 |
|---|---|---|---|---|
| Weight of upper layer (mg) | 165.0 | 330.0 | 100.0 | 125.0 |
| Weight of lower layer (mg) | 520.0 | 520.0 | 520.0 | 520.0 |
| Weight ratio of upper layer:lower layer | 1:3.15 | 1:1.58 | 1:5.20 | 1:4.16 |
| Content uniformity of esomeprazole | 100.7 ± 4.4 | 101.3 ± 2.8 | 100.2 ± 7.2 | 102.2 ± 6.0 |
| Acceptance Value | 10.6 | 6.7 | 17.3 | 15.1 |

Double-layer tablets of Examples 1 and 3 and Comparative Examples 5 and 6 were prepared using the final mixed part of the upper layer and the final mixed part of the lower layer of the same composition ratio, but the total content of the upper final mixed part was different. Accordingly, in each prepared double-layer tablet, the flowability of the final mixed part of the upper layer was the same, and only the weight ratio of the upper layer and the lower layer was different. From the result, the content uniformity difference due to the weight ratio of the upper layer and the lower layer was confirmed.

In Examples 1 and 3, where the weight ratio of the upper layer to the lower layer was about 1:3.2 or less, the acceptance value of the content uniformity was 15 or less, but in Comparative Examples 5 and 6, where the weight ratio of the upper layer to the lower layer was 1:4 or more, the acceptance value of the content uniformity judgment value was 15 or more, which is considered as inappropriate. Even when the total weight is constant during double-layer tablet tableting, the mass deviation of the upper layer may be affected by the mass deviation of the lower layer including antacid, and in fact, it was confirmed that the content uniformity of esomeprazole included in the upper layer was affected by the weight ratio of the upper layer:the lower layer.

Test Example 3: Physical Stability

To evaluate physical stability of formulations, after placing 30 double-layer tablets of each of Examples 1, 4, and 5 in a high density polyethylene (HDPE) bottle and dropping times from a height of 150 cm, breakage of tablets were identified. The results thereof are shown in Table 6.

TABLE 6

| | Example 1 | Example 4 | Example 5 |
|---|---|---|---|
| Length ratio of major axis:minor axis of tablet | 2.07:1 | 1.75:1 | 2.22:1 |
| Number of broken tablets | 0 | 0 | 0 |

As shown in the Table 6, the formulations of Examples 1, 4, and 5 with the length ratio of the major axis:minor axis of the tablets less than about 2.3:1 did not show tablet breakage in the drop test.

From this result, it was confirmed that physical stability of the double-layer tablet having a major axis:minor axis length ratio of about 2.3:1 or less was excellent.

Test Example 4: Dissolution Test of Esomeprazole

Under the following dissolution conditions and analysis conditions, the dissolution rate of esomeprazole from the preparations prepared in Examples 1 to 3 was evaluated, and the results are shown in FIG. 1.

<Dissolution Conditions>

Eluate: 2 tablets (80 mg as esomeprazole) were used in testing with a mixed liquid of 75 mL of 0.1 N HCl and 225 mL of purified water.

Apparatus: the second paddle method of the US Pharmacopoeia (USP) dissolution test item, 75±2 rpm Temperature: 37±0.5° C.

Dissolution time: 5, 10, 15, 30, 45, and 60 minutes (After passing the collected eluate through a 0.45 μM membrane filter, the eluate was immediately mixed well with 0.25 M NaOH at a ratio of 5:1 to use as the sample solution.)

<Analysis Conditions>

Column: Inertsil ODS-3V 150 mm×4.6 mm, 5 μm (Column temperature: 25° C.)

Mobile phase: acetonitrile:phosphate buffer solution (pH 7.3):water=350:500:150

(For the phosphate buffer solution (pH 7.3) in the mobile phase, 10.5 mL of 1 mol/L sodium dihydrogen phosphate and 60.0 mL of 0.5 mol/L disodium hydrogen phosphate were mixed, and water was added thereto up to 1 L.)

Detector: Ultraviolet absorption spectrometer (measurement wavelength: 302 nm)

Flow rate: 1.0 milliliter per minute (mL/min)

Injection amount: 20 μL

Sample temperature: 25° C.

Under these conditions, the eluate was a mixture of 0.1 N HCl and purified water, and the eluate reenacted the mixture of gastric juice present in the stomach and water taken together for drug administration. The eluate was to check the degree of decomposition of esomeprazole and the antacid power of antacid due to the low pH in the stomach when the formulations prepared in Examples 1 to 3 are taken.

FIG. 1 is a graph of dissolution rates (%) of esomeprazole versus dissolution time (minutes) of composite formulations prepared in Examples 1 to 3.

As shown in FIG. 1, the dissolution rate of about 70% or more for 60 minutes in Examples 1 to 3.

From the results, it may be seen that the formulations of Examples 1 to 3 show a sufficient dissolution rate, and the dissolution of esomeprazole by gastric acid is prevented, thereby improving stability and not inhibiting dissolution.

While the present disclosure has been specifically shown and described with reference to preferred embodiments thereof, it will be understood by those skilled in the art that various changes in form and details may be made therein without departing from the spirit and scope of the present disclosure as defined by the appended claims. The disclosed embodiments should be considered in descriptive sense only and not for purposes of limitation. Therefore, the scope of the present disclosure is defined not by the detailed description of the present disclosure but by the appended claims, and all differences within the scope will be construed as being included in the present disclosure.

The invention claimed is:

1. A pharmaceutical composite formulation comprising:

a first layer comprising, as an active ingredient, a proton pump inhibitor or a pharmaceutically acceptable salt thereof, a lubricant, and a binder; and a second layer comprising, as an active ingredient, an antacid that is magnesium hydroxide, wherein the proton pump inhibitor or a pharmaceutically acceptable salt thereof is esomeprazole or a pharmaceutically acceptable salt thereof, wherein the lubricant in the first layer is sodium stearyl fumarate, wherein the lubricant is comprised in an amount of 3.7 percent by weight (wt %) to 5.5 wt % based on the total weight of the first layer, wherein the binder is hydroxypropyl cellulose, wherein the binder is comprised in an amount of 1 wt % to 20 wt % based on the total weight of the first layer, wherein the first layer comprising the proton pump inhibitor or a pharmaceutically acceptable salt thereof, the lubricant, and the binder is in a form of granules, and wherein when a total weight of the first layer is 1 part by weight, a total weight of the second layer is 1.58 to 3.2 parts by weight.

2. The pharmaceutical composite formulation of claim 1, wherein the composite formulation is a tablet or a capsule.

3. The pharmaceutical composite formulation of claim 1, wherein the composite formulation is a double-layer tablet having a length ratio of major axis:minor axis of 1:1 to 2.3:1.

4. The pharmaceutical composite formulation of claim 1, wherein the first layer further comprises any one selected from the group consisting of a diluent, a disintegrant, and any mixture thereof.

5. The pharmaceutical composite formulation of claim 1, wherein the second layer further comprises any one selected from the group consisting of a diluent, a disintegrant, a fluidizing agent, a lubricant, and any mixture thereof.

6. The pharmaceutical composite formulation of claim 1, wherein when a mixed solution of 150 mL of 0.1 N HCl and 450 mL of purified water is tested under conditions of 75 rpm and 37±0.5° C. according to the second paddle method of the US Pharmacopoeia (USP) dissolution test item, a dissolution rate of the proton pump inhibitor for 60 minutes is 55% or higher.

7. A method of preparing the pharmaceutical composite formulation of claim 1, the method comprising:

preparing a first layer mixed part comprising, as an active ingredient, a proton pump inhibitor or a pharmaceutically acceptable salt thereof, a lubricant, and a binder; and preparing a second layer mixed part comprising, as an active ingredient, an antacid that is magnesium hydroxide; and tableting the first layer mixed part and the second layer mixed part, wherein the preparing of the first layer mixed part comprises a granulation process, wherein the proton pump inhibitor or a pharmaceutically acceptable salt thereof is esomeprazole or a pharmaceutically acceptable salt thereof, wherein the lubricant in the first layer is sodium stearyl fumarate, wherein the lubricant is comprised in an amount of 3.7 percent by weight (wt %) to 5.5 wt % based on the total weight of the first layer, wherein the binder is hydroxypropyl cellulose, wherein the binder is comprised in an amount of 1 wt % to 20 wt % based on the total weight of the first layer, wherein the first layer comprising the proton pump inhibitor or a pharmaceutically acceptable salt thereof, the lubricant, and the binder is in a form of granules, and wherein when a total weight of the first layer is 1 part by weight, a total weight of the second layer is 1.58 to 3.2 parts by weight.

* * * * *